United States Patent
Nanini-Maury et al.

(10) Patent No.: US 10,322,270 B2
(45) Date of Patent: Jun. 18, 2019

(54) SKIN CARE APPLICATOR

(71) Applicant: The Procter & Gamble Company, Cincinnati, OH (US)

(72) Inventors: Lucas Boalem Nanini-Maury, Singapore (SG); Jeffrey David Edwards, Perth (AU)

(73) Assignee: The Procter & Gamble Company, Cincinnati, OH (US)

(*) Notice: Subject to any disclaimer, the term of this patent is extended or adjusted under 35 U.S.C. 154(b) by 177 days.

(21) Appl. No.: 14/857,091

(22) Filed: Sep. 17, 2015

(65) Prior Publication Data

US 2016/0074642 A1    Mar. 17, 2016

Related U.S. Application Data

(60) Provisional application No. 62/051,777, filed on Sep. 17, 2014.

(51) Int. Cl.
| | |
|---|---|
| *A61M 35/00* | (2006.01) |
| *A61N 2/06* | (2006.01) |
| *A61M 37/00* | (2006.01) |
| *A61N 2/00* | (2006.01) |
| *A45D 40/28* | (2006.01) |

(52) U.S. Cl.
CPC .......... *A61M 35/003* (2013.01); *A45D 40/28* (2013.01); *A61M 37/00* (2013.01); *A61N 2/002* (2013.01); *A61N 2/06* (2013.01); *A45D 2200/20* (2013.01); *A61M 2037/0007* (2013.01)

(58) Field of Classification Search
CPC ............ A61M 35/003; A61M 37/00; A61M 2037/0007; A45D 40/28; A45D 2200/20; A61N 2/06; A61N 2/002; A61K 2800/47; A61Q 19/10

See application file for complete search history.

(56) References Cited

U.S. PATENT DOCUMENTS

| | | | |
|---|---|---|---|
| 4,046,591 A * | 9/1977 | Laguerre | A61K 8/19 134/1 |
| 5,991,961 A | 11/1999 | Zurik | |
| 6,113,530 A * | 9/2000 | Chien | A61H 39/00 600/9 |
| 6,564,093 B1 | 5/2003 | Ostrow | |
| 7,597,495 B2 | 10/2009 | Gueret | |

(Continued)

FOREIGN PATENT DOCUMENTS

| | | | | |
|---|---|---|---|---|
| JP | 2011083394 A * | 4/2011 | | A61N 2/06 |
| JP | 2013001685 A * | 1/2013 | | |

(Continued)

OTHER PUBLICATIONS

International Search Report PCT/US2015/050625; dated Dec. 8, 2015; 12 pages.

(Continued)

*Primary Examiner* — Kaylee R Wilson
(74) *Attorney, Agent, or Firm* — John G. Powell

(57) ABSTRACT

An applicator for use with a skin care composition, comprising a magnetic element disposed inside the applicator and a cover that at least partially covers the magnetic element. The cover has a thickness of between 0.1 mm and 0.55 mm and is formed of a material having a thermal conductivity of at least 50 W/mK.

17 Claims, 6 Drawing Sheets

(56) References Cited

U.S. PATENT DOCUMENTS

| | | |
|---|---|---|
| 7,608,035 B2 | 10/2009 | Farone |
| 8,019,412 B2 | 9/2011 | Edwards |
| 8,105,228 B2 | 1/2012 | Holcomb |
| 8,316,862 B2 | 11/2012 | Shapiro |
| 2005/0228207 A1* | 10/2005 | Ardizzone ............ A61N 2/002 600/9 |
| 2006/0222689 A1 | 10/2006 | Lin |
| 2007/0053858 A1 | 3/2007 | Bissett |
| 2008/0103350 A1* | 5/2008 | Farone .................. A61N 2/006 600/13 |
| 2009/0003917 A1* | 1/2009 | Duncan ................. A45D 34/04 401/6 |
| 2009/0093669 A1 | 4/2009 | Farone |
| 2011/0077450 A1* | 3/2011 | Yang ....................... A61N 2/06 600/12 |
| 2012/0130150 A1 | 5/2012 | Edwards |
| 2012/0149969 A1 | 6/2012 | Holcomb |
| 2013/0006040 A1 | 1/2013 | Lee |
| 2013/0137063 A1 | 5/2013 | Edwards |
| 2013/0144109 A1 | 6/2013 | Edwards |
| 2013/0303827 A1* | 11/2013 | Feng ....................... A61N 2/06 600/9 |
| 2014/0194668 A1* | 7/2014 | Hanson ................. A61N 2/004 600/9 |
| 2014/0336616 A1 | 11/2014 | Edwards |
| 2015/0150599 A1 | 6/2015 | Matsushita |

FOREIGN PATENT DOCUMENTS

| | | | |
|---|---|---|---|
| JP | WO 2014024629 A1 * | 2/2014 | ............ A61B 17/52 |
| WO | WO2006/097785 | 9/2006 | |
| WO | WO2006131997 A1 | 12/2006 | |
| WO | WO2011/046018 | 4/2011 | |
| WO | WO2011/146977 A1 | 12/2011 | |
| WO | WO2012/031335 A1 | 3/2012 | |

OTHER PUBLICATIONS

International Search Report PCT/US2015/050645; dated Dec. 7, 2015.

International Search Report PCT/US2015/050641; dated Dec. 7, 2015; 8 pages.

U.S. Appl. No. 14/857,010, filed Sep. 17, 2015 Rosemarie NMN Osborne.

U.S. Appl. No. 14/857,028, filed Sep. 17, 2015, Rosemarie NMN, Osborne.

U.S. Appl. No. 14/857,35, filed Sep. 17, 2015, Matthew James, McIldowie.

International Search Report and Written Opinion of the International Searching Authority, PCT/US2015/050641, dated Dec. 7, 2015, 13 pages.

* cited by examiner

SKIN CARE APPLICATOR

FIELD OF THE INVENTION

The present invention relates to an applicator having a magnet disposed therein for use with a skin care composition. The applicator is provided with a cover formed of a material having a thermal conductivity of at least 50 W/mK and a thickness of between 0.1 mm and 5.5 mm.

BACKGROUND OF THE INVENTION

Applicators for use with skin care compositions, for example, facial skin care compositions, are well known. Typically, the applicators are compact in size (for ease of use), are designed to be aesthetically pleasing, and often provide some sensory benefit. Depending on the specific target area of application, the applicator may be formed of different material and/or may have a different shape. For example, applicators for use around the eye are frequently made with rounded edges and of solid metal—the rounded edges provide for smooth application, whereas the solid metal provides a nice cooling effect for the skin.

Some applicators are designed to provide additional benefits. For example, WO 2011/156869 describes a magnetic device used to apply a skin or hair care composition to a user's skin or hair. The magnetic device provides enhanced penetration of certain actives provided in the composition. Various forms of device are described in WO 2011/156869, for example in the form of an adhesive dressing to be applied to skin, or as a brush for application of the composition to hair. In all cases, the device is focused on the technical challenges associated with how best to enable interaction between the magnet embedded in the device and the skin or hair care composition without considering other factors related to application of products to skin.

It is an object of the present invention to provide an applicator that provides multiple benefits of enhancing penetration of actives together with providing an enhanced sensory feel.

SUMMARY OF THE INVENTION

According to a first aspect of the invention, there is provided a skin care applicator comprising a body having a handle and a skin contact tip; a magnet embedded within the body positioned adjacent the skin contact tip, wherein the skin contact tip is formed of a material having a thermal conductivity of greater than 50 W/mL and a thickness of between 0.1 mm and 5.5 mm.

A magnet is provided in the skin care applicator to interact with different skin care compositions, for example by enhancing penetration into skin of different actives within the compositions. For maximum effectiveness of the magnet, it is preferable for the magnet to be positioned as close to the target area of application as possible, in this case a user's skin. Placing the magnet in direct contact with skin provides the required proximity for effective application, but would not provide a pleasant user experience. The skin contact tip has thermally conductive properties that cool down the skin's surface when it makes contact. The thickness of the skin contact tip is optimized to provide sufficient cooling without significantly interfering with the magnetic field generated by the magnet.

The skin contact tip may be formed of a material having a coefficient of friction less than the coefficient of friction of the magnetic substrate from which the magnetic element is formed. This enables the skin contact tip to glide smoothly over a user's skin.

The skin contact tip may be replaceable. This may be desirable where the applicator is to be used for two different users or for multiple different compositions. It may then be preferable to replace the skin contact tip for hygiene reasons.

The skin contact tip may be provided with a round pointed tip, to enable application of skin care compositions in small and hard to reach places, such as near the eye.

In an embodiment, the applicator has an elongate shape with the skin contact tip at one end, and the handle at the other end.

Preferably, the skin contact tip is positioned on one side of the applicator, and the handle extends along the other side, providing additional areas to hold and/or grip the applicator.

The skin contact tip is preferably positioned at one end of the applicator, with the handle located at the other end. In embodiments, the ratio of length of skin contact tip to handle may be 1:3.

In an alternative embodiment, the skin contact tip has a substantially annular shape, and the handle extends away from the skin contact tip at an angle to the skin contact tip.

Preferably, the handle extends away from the skin contact tip in a perpendicular direction.

Preferably the magnetic array is positioned flush with the inside of the skin contact tip to minimize the distance between the magnetic array and the surface on which the applicator is intended to be used.

BRIEF DESCRIPTION OF THE DRAWINGS

Embodiments of the invention will hereinafter be described, by way of example, with reference to the accompanying drawings, in which.

DETAILED DESCRIPTION OF THE INVENTION

Figure 1:
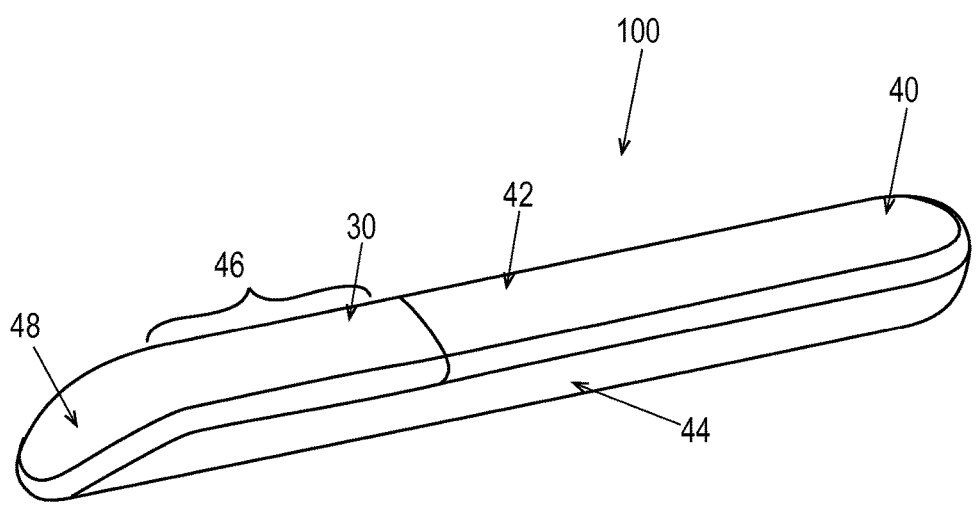
FIG. 1 is a perspective view of an applicator as described herein.

This invention is applicable to applicators comprising one or more magnetic element. The applicator is suitable for either applying a skin care composition to a target portion of skin or for placing above a target portion of skin to which a skin care composition has already been applied. The specific form and ergonomics of the applicator may vary according to the intended target area of application on skin. For example, in some cases, when the skin care composition is a cream intended for application to the whole body, the applicator may be required to apply the cream to large surface body parts, for example, the legs, arms, abdomen and/or back. In this case, the applicator will need to be of a suitable size and shape to enable a user to quickly and easily cover a relatively large surface area. Alternatively, the skin care composition may be intended for use in smaller areas such as the face (e.g., cheeks, forehead, chin, nose, and peri-orbital regions). In such cases, the applicator will need to be smaller to allow more precise application of the skin care composition.

The applicator described herein has at least one magnetic element embedded therein. It is known, for example in WO 2011/156869, that applying a skin care composition using a magnetic element (for example, a dipolar magnetic array) can improve penetration of certain skin care actives into skin by exploiting the unique diamagnetic properties of the skin care actives. Diamagnetism is the property of an object or material which causes it to create a magnetic field in opposition to an externally applied magnetic field, thus causing a repulsive effect. Controlling this repulsive effect, and thereby penetration into skin, requires careful design of the magnetic element or array to ensure compatibility with the target skin care active. As external factors may also affect or influence this repulsive effect, the applicator within which the magnetic element or magnetic array is embedded also requires careful design.

The applicator described herein is provided with a cover that partially or wholly covers the magnetic element embedded within the applicator. The cover may have a thickness of between 0.1 mm and 5.5 mm and a thermal conductivity of at least 50 W/mK. Surprisingly, it has been discovered that providing an applicator with such a cover provides sensory benefits, such as cooling of skin, without negatively impacting diamagnetic repulsion of a compatible skin care active using.

FIGS. 1 to 5 show examples of different applicators 100, 200, 300, 400, all of which have embedded therein a magnetic element 20 (shown in the exploded view of FIG. 2), and a cover 30 that at least partially or wholly covers the magnetic element 20. The cover forms at least part of the skin contact surface of the applicator such that, during use, the cover is positioned between the magnetic element 20 and the target skin surface on which the skin care composition is being applied.

The cover is formed of a material having thermal conductivity of at least 50 W/mK, 100 W/mK or 200 W/mK. The cover described herein acts as a heat sink for the skin's surface, drawing heat away and providing a beneficial cooling effect on the user's skin. The higher the thermal conductivity of a material, the more efficient it will be at transferring heat. However, materials with high conductivity tend to be more expensive and are oftentimes more brittle, thus making them more difficult to manufacture at the thicknesses required herein. Thus, for practical reasons relating to manufacturability, cost and compatibility with the magnetic element, the cover may have a maximum thermal conductivity of up to 500 W/mK, 1000 W/mK, 2000 W/mK or 3000 W/mK.

The cover will generally be formed of material that has higher thermal conductivity than the magnetic substrate from which the magnetic element is formed. The cover may be formed from, for example, a metal, metal alloy, plated metal or plastic (e.g., galvanized, electroplated or vacuum metalized with, for example, chrome, nickel or tin), or loaded plastic (for example, plastic such as PE, PP, PET or ABS, loaded with a material such as metal powder, compounds, minerals (chalk/calcium carbonate/ceramic) or black carbon or graphite), glass, ceramics, etc. For example, the cover may be formed of materials such as aluminium, brass, copper, silver, graphite, diamond, diamond like carbon or combinations thereof.

A suitable cover may, for example, be formed of aluminium or plated aluminium, having a thermal conductivity of approximately 167 W/mK. Using aluminium or plated aluminium additionally provides a desirable aesthetic finish to the cover.

Providing a thick skin contact surface area with high thermal conductivity maximizes the amount of heat transfer from a target area of skin into the applicator, thus also maximizing the cooling benefit during use. Conversely, however, if the cover is made too thick, the cover would interfere with the magnetic field generated by the magnetic element and, as a result, the depth of penetration of a target skin active into skin. It has been found that there is an optimal thickness for the cover where the cover can provide a perceivable cooling effect on skin, without significantly impacting penetration of the skin care active. Thus, the cover has a thickness of from 0.1 mm, 0.15 mm, 0.2 mm, 0.25 mm or 0.3 mm to 0.35 mm, 0.4 mm, 0.5 mm or 0.55 mm.

The skin contact surface of the cover may be substantially flat and/or slightly rounded to provide good thermal contact with skin tissue when in use. For example, when the applicator is intended for use around peri-orbital areas, it is desirable to provide a cover with a slightly rounded and pointed tip, as shown in FIG. 1.

The cover may be permanently joined to the applicator, or the cover may be removable, detachable and/or replaceable. In some instances, the cover may be removed and reattached, for example, to facilitate cleaning the cover and/or applicator. In some instances, the cover may be disposable. For example, the cover may be removed and discarded after one or more uses and replaced with a different cover. The cover may be joined to the applicator by any suitable means known in the art.

It may be desirable for the cover to have a coefficient of friction that is less than that of the magnetic substrate, to provide a more desirable user experience when applying a skin care composition with the applicator. For example, the cover may have a dry coefficient of friction (i.e., a coefficient of friction measured without a composition) that is between 10 and 50% less than the magnetic substrate (e.g., 15%, 20%, 25%, 30%, 35%, 40%, or even 45% less) according to the Friction Test described below. When used to apply a skin care composition, the cover may exhibit a coefficient of friction that is up to 10 times less than the magnetic substrate (for example, between 2× and 10× less, 3× and 7× or even between 4× and 6× less).

The magnetic element is located within the applicator adjacent an inside surface 32 of the cover. The magnetic element may be positioned substantially in parallel to the cover such that, in use, the magnetic element will be substantially parallel to any surface on which the applicator is used. In one example, the magnetic element is positioned flush with the inside surface with no air-gaps between the skin facing side 22 of the magnetic element and the inside face 32 of the cover 30 to minimize losses of magnetic field strength across the cover.

The magnetic element may be formed of any one of numerous known ferromagnetic substrates, including, but not limited to: an iron compound (e.g., a ferrite such as barium ferrite, magnetite, or mild steel), a cobalt material, a strontium material, a barium material, a nickel material, alloys and oxides of these, combinations thereof and the like. The material may have a metalloid component such as boron, carbon, silicon, phosphorous or aluminium. Rare materials such as neodymium or samarium may also be used. A suitable magnetic substrate may be formed of a ferromagnetic material such as strontium ferrite, having a thermal conductivity of approximately 4 W/mK.

The magnetic substrate may be formed of a rigid or flexible material, dependent on the intended use or design of the applicator. For example, where the applicator has one or more curved skin contact surfaces, or is formed as, for example, a roller-ball applicator, the substrate may be formed of a flexible material, such as strontium ferrite impregnated in polyvinyl chloride. Alternatively, where the applicator has a generally flat skin contact surface, the substrate may be formed of a rigid material.

The magnetic element may have an overall magnetic field strength of between 12 mT and 32 mT to enable targeted penetration of compatible skin care actives to a pre-determined layer of skin.

The applicator is optionally provided with a handle. The handle may be formed integrally with and of the same material as the cover. Alternatively, the handle may be formed of a different material to the cover, for example, the plastic, polymeric material or ceramic. In an example, the cover may be formed of polyvinyl chloride or rubber to provide a nice tactile handle for use during application of the skin care composition.

The applicator shown in FIG. 1 has an elongate handle 40. The cover forms an extension of the handle on a skin contact side 42 of the handle, whereas the handle extends the length of the applicator on the reverse side 44. In such an embodiment, a user may hold the handle in the palm of their hand and rest their finger on the reverse side of the applicator to provide better control and precision during use of the applicator. The cover is provided with a substantially elongate flat section 46, intended for use on larger, flatter surfaces of human skin, and a curved section at a tip 48 for use in smaller areas, for example, in peri-orbital areas. The ratio of length of substantially flat section to curved tip is between 1:1, 3:2 or 2:1. Elongate sides 50 of the handle 40 and cover 30 are also curved to provide a more refined looking and tactile feeling applicator. The applicator shown in FIG. 1 has a length $l_a$ from 50 mm, 60 mm or 70 mm to 80 mm, 90 mm or 100 mm. The cover has a length $l_c$ from 15 mm, 25 mm, or 30 mm to 35 mm, 40 mm or 45 mm. In an example, the ratio of length of the handle to cover is between 4:1, 3:1 and 2:1.

Figure 2:
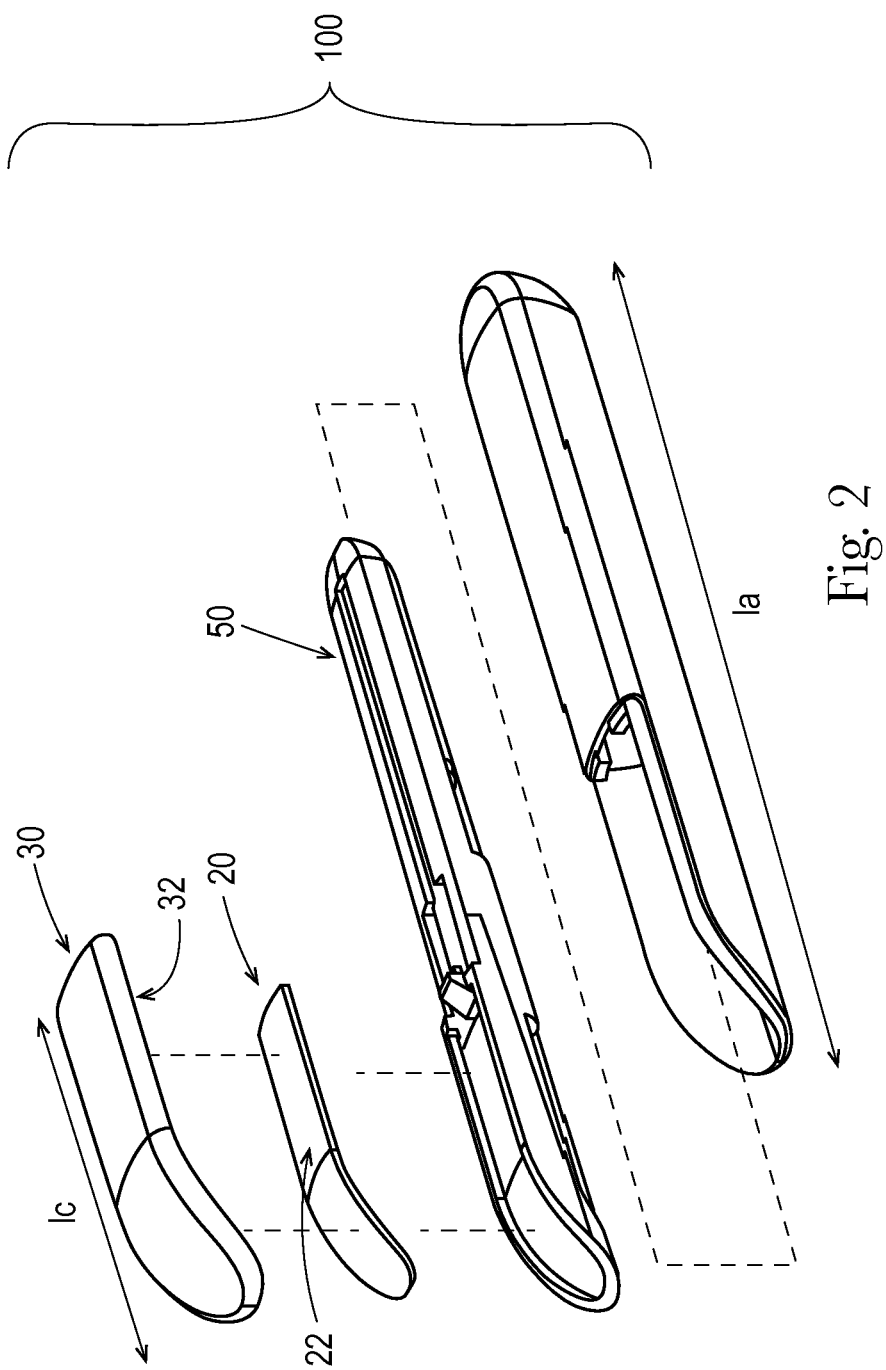
FIG. 2 is an exploded view of the applicator of FIG. 1.

As shown in FIG. 2, the applicator is additionally provided with an insert 50 that forms the central structure of the applicator. The insert may be formed of any known material, for example plastic or metal, which can preferably easily be molded. The magnetic element is adhered to the insert and the cover positioned above the magnetic element. The cover may be fixed in place above the magnetic element using any known adhesive. The handle 40 forms a shell around the central insert.

Figure 3:
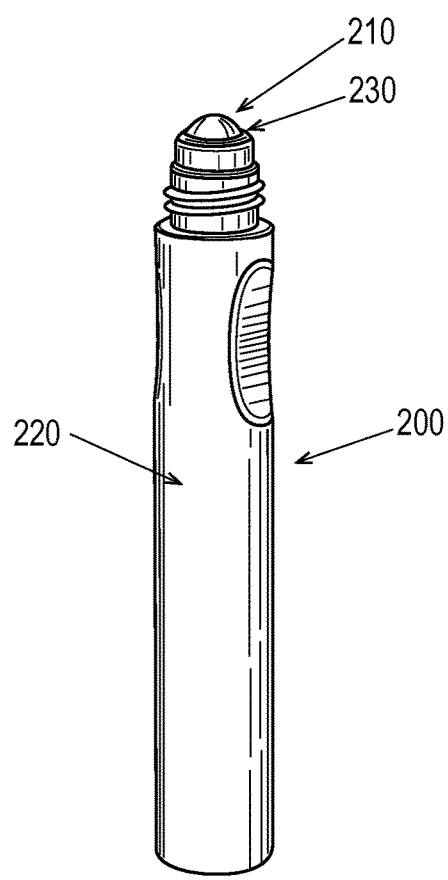
FIG. 3 is a perspective view of an alternative applicator.

An alternative form of applicator 200, shown in FIG. 3, has a rounded tip 210 that may be suitable for use around the eye. The rounded tip may be integrally formed with the handle 220, or it may be formed as a rotatable ball held within a socket 230 at the end of the handle. The magnetic element (not shown) may be disposed inside the rounded tip, such that as the tip is rolled over a surface of skin, the magnetic element will remain substantially in parallel to the target surface of skin. In this case, the tip functions as the cover.

Figure 4:
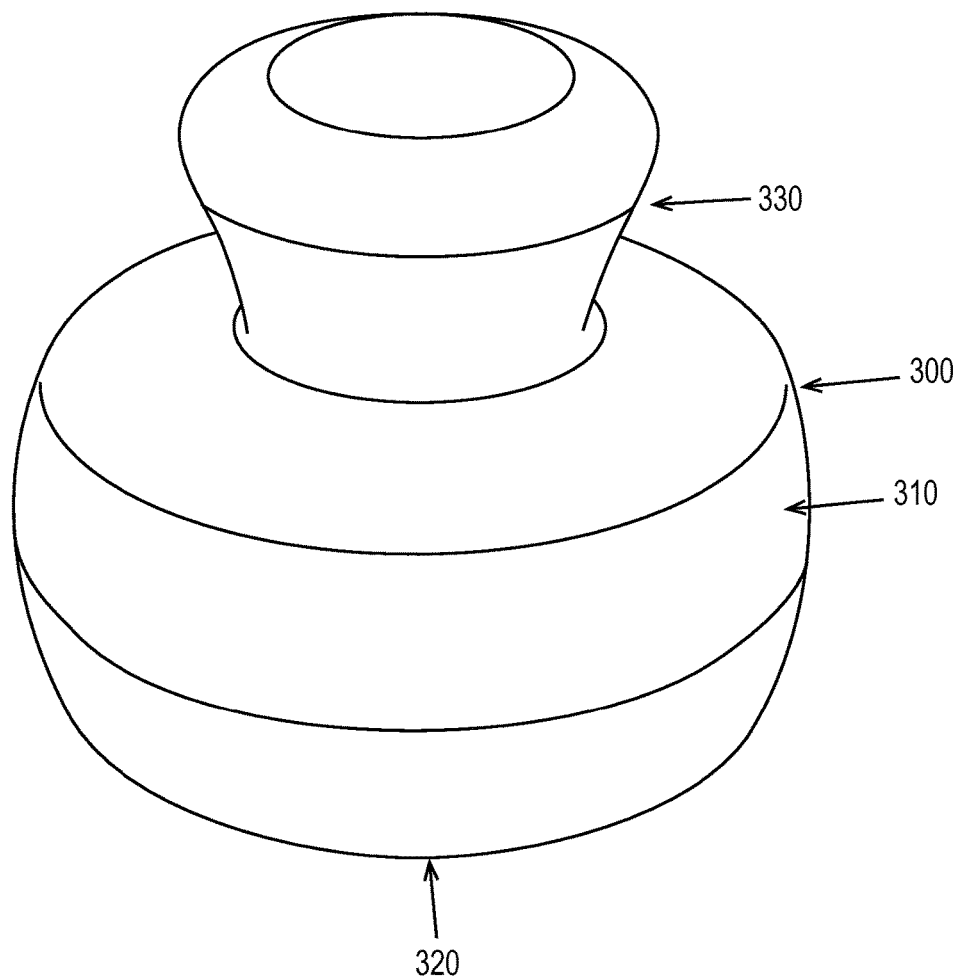
FIG. 4 is a perspective view of an alternative applicator.

The applicator shown in FIG. 4 has a substantially annular base 310 with the cover 320 extending across the bottom of the base. The handle 330 extends from the base in a direction substantially perpendicular to the skin contact surface of the cover. The magnetic element (not shown) is disposed inside the base, adjacent to and in parallel with the skin contact surface of the cover so that, in use, the magnetic element will be substantially parallel to the target surface of skin.

Figure 5:
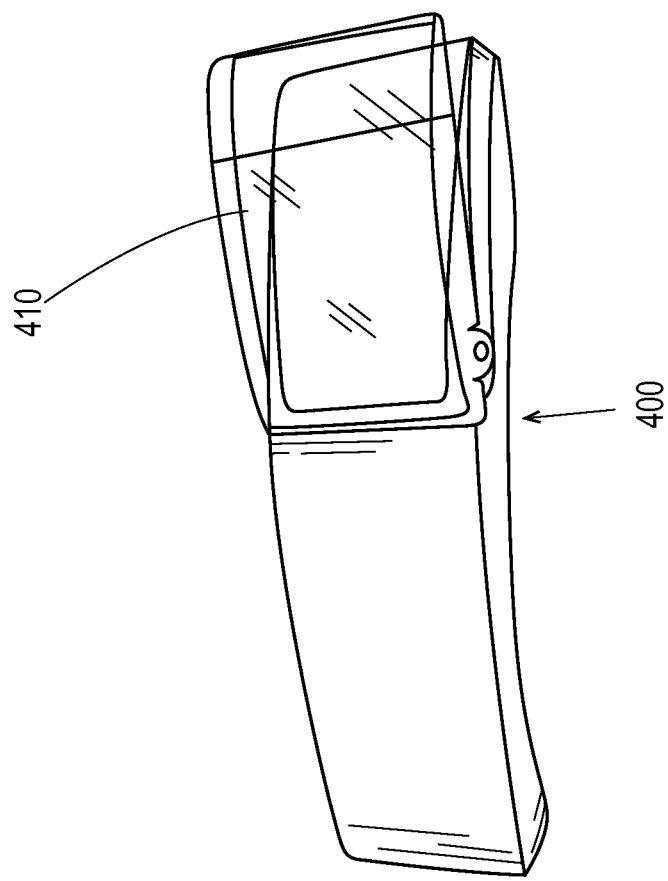
FIG. 5 is a perspective view of a further alternative applicator.

The applicator shown in FIG. 5 includes a removable cover 410 with a larger surface area. The applicators shown in FIG. 4 and FIG. 5 are generally intended for use on larger surface areas, e.g. arms/legs/cheeks.

It will be appreciated that although the covers shown herein are generally rectangular or annular in shape, the cover may be formed in a number of different shapes, for example, triangular, square, oval etc. Furthermore, although the handle is shown generally in parallel with or perpendicular to the cover, the handle could extend in a number of different ways. For example, the handle of the applicator shown in FIG. 5 could extend away from the base at an angle of less or more than 90°.

In use, a user should be able to hold the handle and should have an appropriately sized and shaped skin contact surface with which to either apply a composition or to smooth over skin after application of a skin care composition.

The cover may be transparent to enable a user to see the magnetic element situated beneath the cover. The magnetic element may be attached to the cover by any known means, for example, using adhesive. Alternatively, the magnetic element may be secured in place by the cover.

Coefficient of Friction Method

This method provides a means to determine the coefficient of friction of material surfaces herein. Wet coefficient of friction refers to the coefficient of friction measured on a surface on which a skin care composition is present. Dry coefficient of friction refers to the coefficient of friction measured on a surface on which a skin care composition is not present.

Coefficient of friction is the ratio of the force of friction between two bodies and the force pressing them together. In the present method, the instrument used to determine the coefficient of friction is a Bruker® UMT-2 tribometer. However, an equivalent tribometer may be used, as desired. A purple nitrile glove material is used as one of the two materials in the test. The other material the test surface (e.g., skin contacting surface of the applicator or cover). The purple nitrile glove material is placed over the probe of the tribometer. The test surface to be measured is placed in contact with the nitrile-covered probe of the instrument, and the force is measured according to the manufacturer's operating instructions for the instrument.

Figure 6:
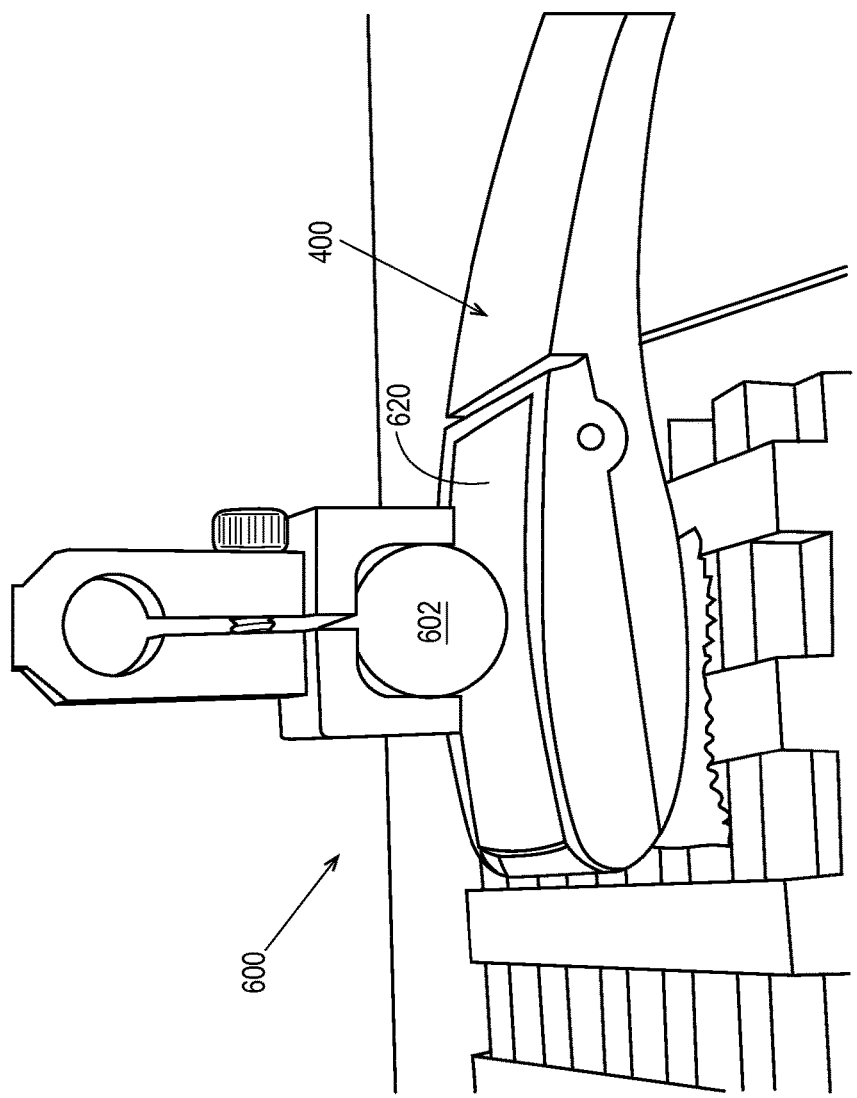
FIG. 6 shows the system used to measure coefficient of friction.

FIG. 6 illustrates the system 600 used to measure coefficient of friction in this example. As shown in FIG. 6, a probe 602 covered with purple nitrile glove material is contacted with the skin-contacting surface 620 of an applicator 400. In this example, the cover has been removed from the applicator 400 and the magnetic array provides the skin-contacting surface 620. The skin-contacting surface of the cover (not shown) was also measured. Both the applicator surface 620 and the cover were tested with and without a skin care composition (Olay ProX Deep Wrinkle Cream available from the Procter & Gamble Co., Ohio). For measuring wet coefficient of friction, 0.1 g of the skin care composition was spread over the test surface. The rate of the probe was set to 1 mm/sec with a force of 100 grams.

Each leg of the test was repeated three times. The coefficient of friction results are shown in Table 13 below.

TABLE 13

| Surface | Coefficient of Friction | | | |
| --- | --- | --- | --- | --- |
| | 1 | 2 | 3 | Avg. |
| Applicator surface (dry) | 1.90 | 1.97 | 1.86 | 1.91 |
| Applicator surface (wet) | 0.45 | 0.62 | 0.45 | 0.50 |
| Cover surface (dry) | 0.77 | 0.96 | 1.09 | 0.94 |
| Cover surface (wet) | 0.06 | 0.06 | 0.06 | 0.06 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator for use with a skin care composition, comprising:
   a) a magnetic element that has an overall magnetic field strength of between 12 mT and 32 mT;
   b) a cover that at least partially covers the magnetic element, wherein the cover has a thickness of between 0.1 mm and 0.55 mm, is formed of a material having a thermal conductivity of at least 50 W/mK; and
   c) an applicator body, wherein the magnetic element, the cover, and the applicator body each comprise a substantially elongate flat section and a curved tip which are fitted together such that the curved tip of the magnetic element is contiguous with the curved tip of each of the cover and the applicator body to form the applicator.

2. An applicator as claimed in claim 1, wherein the cover is formed of metal.

3. An applicator as claimed in claim 1, wherein the magnetic element is formed of a magnetic substrate having a skin facing side positioned substantially in parallel with an inside surface of the cover.

4. An applicator as claimed in claim 3, wherein the skin facing side of the magnetic substrate lies flush with the inside surface of the cover.

5. An applicator as claimed in claim 3, wherein a skin facing side of the cover has a lower co-efficient of friction than the skin facing side of the magnetic substrate.

6. An applicator as claimed in claim 3, wherein the thermal conductivity of the cover is greater than a thermal conductivity of the magnetic substrate.

7. An applicator as claimed in claim 3, wherein the cover exhibits a coefficient of friction that is up to 10 times less than that of the magnetic substrate.

8. An applicator as claimed in claim 3, wherein the magnetic substrate is formed of strontium ferrite and the cover is formed of aluminium.

9. An applicator as claimed in claim 8, wherein the cover is formed of plated aluminium.

10. An applicator as claimed in claim 1, wherein the cover is removable.

11. An applicator as claimed in claim 1, wherein the cover extends over the curved tip of the applicator body.

12. An applicator as claimed in claim 1, further comprising a handle formed integrally with the cover.

13. An applicator as claimed in claim 12, wherein the applicator has an elongate shape and a ratio of length of handle to cover on the skin contact side of the applicator is between 1:1 and 4:1.

14. An applicator as claimed in claim 12, wherein the handle is formed of polyvinyl chloride.

15. An applicator as claimed in claim 1, wherein the magnetic element is a magnetic array formed of one or more dipole pairs of alternating north and south poles.

16. The applicator of claim 1, wherein a ratio of length of the substantially flat section to the curved tip is between 1:1 and 2:1.

17. The Applicator of claim 1, wherein the magnetic element is disposed between the cover and the applicator body in a sandwich configuration.

* * * * *